United States Patent [19]

Röhrscheid et al.

[11] Patent Number: 5,202,469

[45] Date of Patent: Apr. 13, 1993

[54] PARTIALLY FLUORINATED DICARBOXYLIC ACID AND THE ACID CHLORIDE THEREOF, AND A PROCESS FOR THEIR PREPARATION

[75] Inventors: Freimund Röhrscheid; Wolfgang Appel, both of Kelkheim; Günter Siegemund, Hofheim, all of Fed. Rep. of Germany

[73] Assignee: Hoechst Aktiengesellschaft, Frankfurt am Main, Fed. Rep. of Germany

[21] Appl. No.: 718,009

[22] Filed: Jun. 20, 1991

[30] Foreign Application Priority Data

Jun. 25, 1990 [DE] Fed. Rep. of Germany ....... 4020185

[51] Int. Cl.$^5$ ............... C07C 51/265; C07C 51/60; C07C 63/331
[52] U.S. Cl. ........................... 562/416; 560/77; 560/83; 562/417; 562/488; 562/853; 562/862
[58] Field of Search ............ 560/77, 83; 562/416, 562/417, 488, 853, 862

[56] References Cited

U.S. PATENT DOCUMENTS

| | | | |
|---|---|---|---|
| 3,355,500 | 11/1967 | Farah et al. | 568/637 |
| 4,339,595 | 7/1982 | Udovich et al. | 560/76 |
| 4,433,132 | 2/1984 | Rogers et al. | 528/191 |
| 4,716,245 | 12/1987 | Hirose | 562/416 |
| 4,758,380 | 7/1988 | Alston et al. | 562/488 X |
| 4,863,640 | 9/1989 | Scola | 549/241 |
| 4,939,305 | 7/1990 | Stenzenberger et al. | 560/83 X |
| 4,950,786 | 8/1990 | Sanchez et al. | 562/416 |

FOREIGN PATENT DOCUMENTS 0063874 11/1982 European Pat. Off. .
0285160 10/1988 European Pat. Off. .
3739797 6/1989 Fed. Rep. of Germany .

OTHER PUBLICATIONS

Farah, B. S. et al, *J. Org. Chem.* 30:998–1001, (1965).
Colon, I. et al, *J. Org. Chem.* 51:2627–2637, (1986).

*Primary Examiner*—José G. Dees
*Assistant Examiner*—Vera C. Clarke
*Attorney, Agent, or Firm*—Connolly & Hutz

[57] ABSTRACT

Partially fluorinated dicarboxylic acid and the acid chloride thereof, a process for its preparation and its use.

The compound of the formula (I)

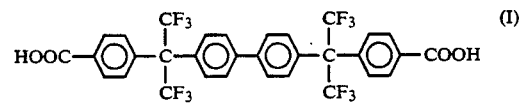

and the acid chloride thereof are prepared by air oxidation in the presence of a catalyst mixture composed of the ions of cobalt, manganese and bromine in an acid organic medium. The compounds can be used for the preparation of linear polycarboxamides and polycarboxylic acid esters.

25 Claims, No Drawings

PARTIALLY FLUORINATED DICARBOXYLIC ACID AND THE ACID CHLORIDE THEREOF, AND A PROCESS FOR THEIR PREPARATION

DESCRIPTION

The invention relates to a partially fluorinated dicarboxylic acid, particularly 4,4'-bis-[2-(4-carboxyphenyl)-hexafluoroisopropyl]-biphenyl, to the acid chloride thereof, to a process for its preparation and its use.

Aromatic dicarboxylic acid halides which, according to a general formula having several variables, can also contain partially fluorinated biphenyls, are known as reactants for the preparation of polyketones in the presence of fluoroalkanesulfonic acids EP-A 0,063,874]. A process for the preparation of the dicarboxylic acid halides is not disclosed. In addition, no dicarboxylic acid halides which are partially fluorinated or contain biphenyl groups are described in the examples.

Partially fluorinated dicarboxylic acids having a diphenyl ether bridge are also known; these have been prepared by air oxidation in an acid medium at an elevated pressure and an elevated temperature in the presence of a catalyst mixture [DE-A 3,739,797].

The invention relates to a compound of the formula

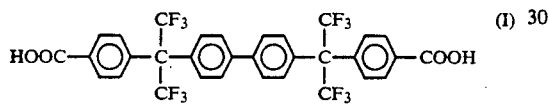

and to the acid chloride thereof, to a process for its preparation and to its use as a monomer component for the preparation of polycondensates, such as polyesters or polyamides.

The preparation of the compound according to the invention is effected by oxidizing the 4,4'-bis-[2-(4-alkylphenyl)-hexafluoroisopropyl]-biphenyl with molecular oxygen in an acid organic medium, the acid medium being composed of at least 40% by weight of a monocarboxylic acid having 1 to 4 carbon atoms, in particular acetic or propionic acid or mixtures thereof, in the presence of a catalyst combination of the ions of cobalt, manganese and bromine. Cerium ions can also be present in addition. Acetic acid is to be preferred because of its greater resistance to oxidative degradation. The ratio of acid medium to the biphenyl compound to be oxidized can be up to 40:60% by weight, relative to the total reaction mass.

The biphenyl compound employed,

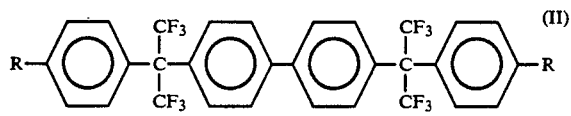

in which R is lower alkyl having 1–4 carbon atoms, alkyl being preferably methyl, ethyl and isopropyl, particularly methyl, is generally prepared by three different methods, namely:

(a) by condensation of one mole of a dicarbinol of the formula

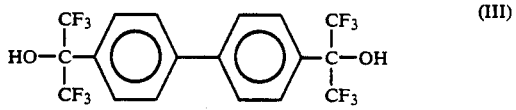

with at least 2 mp; of a compound of the formula

in which R has the meaning mentioned above, or (b) by condensation of at least 2 mol of a compound of the formula

with one mole of biphenyl (VI), in each case in the presence of hydrogen fluoride, or (c) by formation of the carbon-carbon bond between two identical partially fluorinated aromatic compounds of the formula

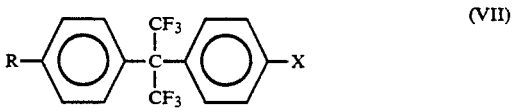

in which R has the meaning mentioned above, by a process known from the literature which is suitable for the formation of aryl-aryl bonds, for example J. Org. Chem. 51, 2627 (1986). X is halogen, preferably chlorine.

Compounds of the formula (III) which are employed in process a), are described in U.S. Pat. No. 3,355,500 and in J. Org Chem. 30, 998 (1965). Compounds of the formula (V) which are reacted by method b) to give the compounds according to formula (II) are also described in J. Org. Chem. 30, 998–1001 (1965).

The reaction according to method a) and b) is carried out at a temperature of 80° to 180° C., preferably 100° to 160° C.

A period of 20 to 90 hours, preferably 40 to 70 hours, is necessary for the reaction according to methods (a) and (b).

The molar ratio of the reactants employed is determined in the case of method a) by the ratio of the compound (III) to compound (IV), and in the case of method (b) by the ratio of the biphenyl to compound (V); it is in each case at least 1:2, preferably 1:2.2 to 1:4.4.

The proportion of hydrogen fluoride necessary in the case of the reaction for the preparation of the compounds method a), to the compound (III) and is, in general, a molar ratio of 1:7 to 1:25, preferably 1:8 to 1:12. In the case of method b) the molar ratio of the compounds (V) to hydrogen fluoride is generally 1:6 to 1:15, preferably 1:8 to 1:12.

The reaction product is generally worked up by removing the hydrogen fluoride from the reactor in the form of gas at approx. 80° C. after the completion of the reaction, and by removing the residue remaining, if appropriate after dilution with an organic solvent, from the reactor, preferably at a temperature of 20° to 30° C.

Suitable solvents which can be used here are aliphatic hydrocarbons having 5 to 10 carbon atoms, aromatic hydrocarbons having 6 to 8 carbon atoms and monochlorinated or polychlorinated aliphatic hydrocarbons having 1 to 4 carbon atoms in the alkyl radical. Examples of these are n-hexane, n-heptane, toluene, the various xylenes, and methylene dichloride and chloroform, preferably toluene, methylene dichloride or chloroform.

The crude mixture obtained is mixed with water, washed and separated off. In general, the purified products are obtained in the form of colorless crystals.

The reaction product can be purified further by being subjected to recrystallization from an organic solvent or it is extracted by stirring in organic solvents, preferably isopropanol, methanol or 1-chloropropane.

The preparation of the compounds according to formula (VII) is possible, by known processes, from compounds of the formula (V) and aryl halides.

The formation of the aryl-aryl bond between two components of the formula (VII) is carried out in a polar, aprotic solvent, such as dimethylacetamide or dimethylformamide, in the presence of a mixture of 1 to 10 mol %, preferably 3 to 6 mol %, of a nickel(II) salt, preferably $NiCl_2$ or $NiBr_2$, and 5 to 40 mol %, preferably 20 to 30 mol %, of an organic phosphorus(III) compound, preferably triphenylphosphine, and zinc powder in an amount of 120 to 160 mol %, relative to the aryl halide employed.

The reaction is carried out in an inert gas atmosphere, particularly an atmosphere of nitrogen or argon, at a temperature of 40 to 80° C.; the reaction takes 2 to 8 hours.

The solid fraction is filtered off and the filtrate is washed several times with water after the addition of a water-immiscible solvent, for example a monochlorinated or polychlorinated aliphatic hydrocarbon having 1-4 carbon atoms in the alkyl radical, in particular methylene dichloride or chloroform, ethyl acetate or diethyl ether. A phase separation is thus set up. After the organic phase has been dried the solvent is distilled off and the residual product is purified by recrystallization.

Bromine are absolutely necessary for the oxidation to run its full course. The two heavy metal salts, particularly those of cobalt and manganese, are generally employed in a ratio of 3:1 to 1:3, preferably 1:1. The sum of the concentrations of the two cations is generally 0.01 to 0.2, preferably 0.02 to 0.12 and especially 0.04 to 0.08, gram atom/kg of total mass. The ratio of the sum of the metal salts, in this case those of cobalt and manganese, to bromine is generally 1:0.01 to 1:2, preferably 1:0.025 to 1:1 and particularly 1:0.05 to 1:0.2.

It is also possible to employ cerium ions in addition to the two metal ions of the catalyst. The cerium ions catalyze the oxidation of incompletely oxidized intermediate stages. Their presence increases the purity and the yield of the partially fluorinated dicarboxylic acid. The cerium ions are added to the catalyst in a ratio of the sum of the cobalt and manganese ions to cerium ions such as 1:0.02 to 1:2, preferably 1:0.05 to 1:1 and particularly 1:0.2 to 1:0.6. The metal salts employed are preferably the corresponding acetates.

Bromine can be employed in the form of bromides, for example the bromides of the alkali metals, including ammonium bromide, and of the metals cobalt, manganese and cerium, or as a solution of hydrogen bromide in water or glacial acetic acid. It is also possible to use organic compounds containing bromine which decompose during the oxidation and liberate bromine ions, for example carbon tetrabromide.

The oxidation is generally carried out at a temperature of 120° to 220° C., preferably 140° to 190° C. and in particular 155° to 180° C. The pressure in the reactor is generally 5 to 40, preferably 10 to 30 and in particular 14 to 20, bar.

It is advantageous for the procedure according to the invention that the air required for the oxidation should be introduced into the liquid phase near the base of the reactor and it should preferably be finely divided by vigorous stirring or by special jets in the liquid phase. It is particularly advantageous to introduce an oxidation mixture, the oxygen content of which has been increased to a proportion of over 21% by volume by admixture of pure oxygen. High partial pressures of oxygen are obtained in the gas bubbles entering the liquid phase by means of this measure. It is advantageous if the partial pressure of oxygen at the outlet point of the introduction device is at least 1 bar, preferably 2 to 15 and particularly 3 to 10 bar.

It is also advantageous for carrying out the process that the residual oxygen content of the exit gas should not fall below specific values. The partial pressure of oxygen is defined by the formula $$P_{O_2} = \% \text{ by volume of } O_2 \cdot (P_{total} - P_{ac})$$

i.e. it is the mathematical product of the residual oxygen content and the difference between the total pressure and the vapor pressure of acetic acid at the ambient reaction temperature. This partial pressure of oxygen in the gas phase over the reaction solution should not fall below 0.2 bar and is preferably 0.35 to 2.8 bar, in particular 0.45 to 1.3 bar.

The dicarboxylic acid obtained in the process according to the invention is converted into the acid chloride in a known manner by treatment with thionyl chloride and is isolated from the reaction solution by known methods.

The compounds according to the invention are used above all for the preparation of linear polycarboxamides and polycarboxylic acid esters which, in the form of shaped articles, films and fibers, have a high heat stability, excellent mechanical properties, good transparency and good soil-repellent properties and resistance to radiation.

EXAMPLES (1) 4,4'-Bis-[2-(4-carboxyphenyl)-hexafluoroisopropyl]-biphenyl 158.6 g of 4,4'-bis[2-(4-methylphenyl)hexafluoroisopropyl-biphenyl, 4.96 g of $Co(OAc)_2 \cdot 4H_2O$, 2.45 g of $Mn(OAc)_2 \cdot 4H_2O$, 2.4 g of HBr=24 g of a 10% strength solution of HBr in glacial acetic acid and 500 g of glacial acetic acid were initially placed in a one-liter glass autoclave equipped with a stirrer, a gas inlet tube, a thermometer, a reflux condenser and an instrument for measuring oxygen in the exit gas line. The reaction mixture was heated to 150° C. under a pressure of 16 bar of nitrogen. After the introduction of air through the inlet tube located near to the base, the exothermic reaction set in immediately with the absorption of oxygen, the temperature rising to 170°-175° C. Sufficient air was introduced for the residual oxygen content in the exit gas to be between 5 and 9% by volume.

The exothermic reaction lasted for 20 minutes. The admission of air was then replaced by a nitrogen-oxygen (9:1) mixture, and the temperature was kept at 165° C. for a further 40 minutes by heating.

The cooled (approx. 115° C.) reaction solution was passed by suction into a two-liter flask and was cooled to 20° C. with stirring. The resulting suspension of crystals was filtered with suction. The filter cake was washed five times with each time 50 ml of glacial acetic acid. The moist product was dried in a gentle stream of air at 70° C./65 mbar.

Yield: 159.9 g (92.1% of theory)
Melting point: 292°-294° C.

A further 7.3 g of dicarboxylic acid (4.2% of theory) were precipitated by concentrating the mother liquor to 70 g.

Melting point: 285°-289° C.

| Analysis for $C_{32}H_{18}F_{12}O_4$: | | | |
|---|---|---|---|
| calculated: | C 55.34% | H 2.61% | F 32.83% |
| found: | C 55.4% | H 2.7% | F 32.6% |

(2)
4,4'-Bis-[2-(4-chlorocarbonylphenyl)-hexafluoroisopropyl]-biphenyl

A few drops of dimethylformamide were added to a suspension of 4,4'-bis-[2-(4-carboxyphenyl)-hexafluoroisopropyl]-biphenyl in thioyl chloride, and the mixture was heated under reflux conditions until the evolution of gas was complete. The excess of thionyl chloride was stripped of and toluene was added in order to remove the residual thionyl chloride by distillation. After the toluene had been removed, the crude product was recrystallized from n-hexane.

Melting point: 154°-158° C.

We claim:
1. A compound of the formula

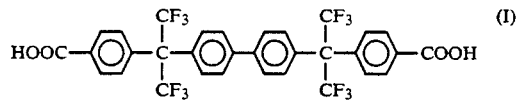

and the acid chloride thereof.

2. A process for the preparation of a compound of the formula

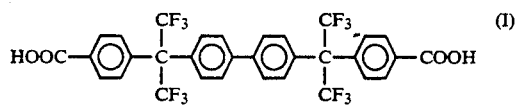

or the acid chloride thereof by air oxidation in an acid medium under elevated pressure and at an elevated temperature in the presence of a catalyst mixture, which comprises oxidizing 4,4'-bis-[2-(4-methylphenyl)-hexafluoroisopropyl -biphenyl by introducing aerial oxygen into an aqueous acidic medium composed of a monocarboxylic acid having 1 to 4 carbon atoms at a temperature of 120° to 220° C. and under a pressure of 5 to 40 bar in the presence of a mixture of compounds of the metals Co and Mn and bromine ions, and isolating the product according to formula (I) or converting the latter into the acid chloride of the compound of the formula (I) using thionyl chloride.

3. The process as claimed in claim 2, wherein the aqueous acidic medium is composed of at least 40% by weight of acetic acid and/or propionic acid, relative to the total weight.

4. The process as claimed in claim 2, wherein the reaction temperature is 140° to 190° C.

5. The process as claimed in claim 2, wherein the oxidation is carried out under a pressure of 10 to 30 bar.

6. The process as claimed in claim 2, wherein the aerial oxygen employed for the oxidation has an oxygen content of over 21% by volume and the partial pressure of oxygen at the inlet point of the oxygen is at least 1 bar.

7. The process as claimed in claim 2, wherein the partial pressure of oxygen in the gas phase above the reaction medium is at least 0.2 bar.

8. The process as claimed in claim 2, wherein the ratio of cobalt to manganese is 3:1 to 1:3.

9. The process as claimed in claim 2, wherein the ratio of the sum of cobalt and manganese to bromine is 1:0.01 to 1:2.

10. The process as claimed in claim 2, wherein cerium is present in the catalyst, the molar ratio of the sum of cobalt and manganese to cerium being 1:0.02 to 1:2.

11. The process as claimed in claim 10, wherein the metal compounds are metal salts.

12. The process as claimed in claim 2, wherein bromine is empolyed in the form of bromides or as a solution of hydrogen bromide in water or glacial acetic acid.

13. The process as claimed in claim 11, wherein the metal salts are acetate.

14. The process as claimed in claim 2, wherein the reaction temperature is 155° to 180° C.

15. The process as claimed in claim 2, wherein the oxidation is carried out under a pressure of 14 to 20 bar.

16. The process as claimed in claim 2, wherein the aerial oxygen employed for the oxidation has an oxygen content. of over 21% by volume and the partial pressure of oxygen at the inlet point of the oxygen is 2 to 15 bar.

17. The process as claimed in claim 2, wherein the aerial oxygen employed for the oxidation has an oxygen content of over 21% by volume and the partial pressure of oxygen at the inlet point of the oxygen is 3 to 10 bar.

18. The process as claimed in claim 2, wherein the partial pressure of oxygen in the gas phase above the reaction medium is 0.35 to 2.8 bar.

19. The process as claimed in claim 2, wherein the partial pressure of oxygen in the gas phase above the reaction medium is 0.45 to 1.3 bar.

20. The process as claimed in claim 2, wherein the ratio of cobalt to manganese is the sum of the concentrations of the two elements cobalt and manganese being 0.02 to 0.12 grams atom/kg of total reaction mass.

21. The process as claimed in claim 2, wherein the ratio of cobalt to manganese is the sum of the concentrations of the two elements cobalt and manganese being 0.04 to 0.08 gram atom/kg of total reaction mass.

22. The process as claimed in claim 2, wherein the ratio of the sum of cobalt and manganese to bromine is 1:0.025 to 1:1.

23. The process as claimed in claim 2, wherein the ratio of the sum of cobalt and manganese to bromine is 1:0.05 is 1:0.2.

24. The process as claimed in claim 2, wherein cerium is present in the catalyst the molar ratio of the sum of cobalt and manganese to cerium being 1:0.05 to 1:1.

25. The process as claimed in claim 2, wherein cerium is present in the catalyst the molar ratio of the sum of cobalt and manganese to cerium being 1:0.2 to 1:0.6.

* * * * *